United States Patent
Steele et al.

(10) Patent No.: US 12,208,286 B2
(45) Date of Patent: Jan. 28, 2025

(54) PARTICLE THERAPY CLOSED-LOOP FEEDBACK SPOT-WISE BEAM CURRENT CONTROL SYSTEMS AND METHODS

(71) Applicant: Varian Medical Systems Particle Therapy GmbH & Co. KG, Troisdorf (DE)

(72) Inventors: Jay Steele, Milpitas, CA (US); Manuel Schedler, Bonn (DE)

(73) Assignee: VARIAN MEDICAL SYSTEMS PARTICLE THERAPY GMBH & CO. KG, Troisdorf (DE)

( * ) Notice: Subject to any disclaimer, the term of this patent is extended or adjusted under 35 U.S.C. 154(b) by 368 days.

(21) Appl. No.: 17/572,447

(22) Filed: Jan. 10, 2022

(65) Prior Publication Data
US 2023/0218927 A1    Jul. 13, 2023

(51) Int. Cl.
*A61N 5/10*    (2006.01)

(52) U.S. Cl.
CPC ......... *A61N 5/1067* (2013.01); *A61N 5/1071* (2013.01); *A61N 2005/1072* (2013.01)

(58) Field of Classification Search
None
See application file for complete search history.

(56) References Cited

U.S. PATENT DOCUMENTS

| | | | |
|---|---|---|---|
| 11,198,022 B1 * | 12/2021 | Tansho | A61N 5/1077 |
| 2010/0171447 A1 | 7/2010 | Balakin | |
| 2013/0023716 A1 * | 1/2013 | Thomas | A61N 5/1071 600/1 |
| 2017/0043183 A1 * | 2/2017 | Balakin | A61N 5/1082 |
| 2019/0022417 A1 | 1/2019 | Heese | |
| 2021/0031056 A1 * | 2/2021 | Inoue | A61N 5/1043 |

FOREIGN PATENT DOCUMENTS

WO    WO-2012/149044 A2    11/2012

OTHER PUBLICATIONS

K.P. Nesteruk et al., "Commissioning of a clinical pencil beam scanning proton therapy unit for ultrahigh dose rates (FLASH)," Arvix.org, Cornell University Library, 201 Olin Library, Cornell University, Ithaca, NY, 14853, Jan. 5, 2021.

* cited by examiner

*Primary Examiner* — Eliza W Osenbaugh-Stewart
(74) *Attorney, Agent, or Firm* — Harness, Dickey & Pierce, P.L.C.

(57) ABSTRACT

Techniques for closed-loop feedback beam control in particle therapy delivery system can include receiving treatment plan beam parameters, receiving a determined output beam current of a present spot, generating an adjusted source beam current set point based on the treatment plan beam parameters and the determined output beam current of the present spot, and adjusting an output beam current of the present spot based on the adjusted source beam current.

19 Claims, 5 Drawing Sheets

PARTICLE THERAPY CLOSED-LOOP FEEDBACK SPOT-WISE BEAM CURRENT CONTROL SYSTEMS AND METHODS

BACKGROUND OF THE INVENTION

Particle therapy can be used in the treatment of cancer, tumors, lesions, and the like. Particle therapy involves directing a beam of high energy charged particles (e.g., ions, protons, or electrons) into a target volume so that their energy is released into the target volume for therapeutic purposes. One of the goals of particle therapy treatment is to maximize the dose energy supplied to a target, such as a tumor, while minimizing the dose energy absorbed by the surrounding tissue. A treatment plan is used to specify various aspects of the particle therapy to deliver sufficient energy to unhealthy tissue in the target volume, while minimizing exposure of surrounding healthy tissue. Important parameters for consideration are the dose delivered in a given treatment volume (particle energy delivered divided by mass of the volume) and dose rate (dose delivered divided by time). The dose can be proportional to a number of monitor units (MUs) measured by an ionization chamber for a particular particle energy and air density. The delivered dose rate for the given treatment volume can be determined from a measured particle beam current and the beam profile, given the energy delivered per particle. The dose rate can be proportional to MUs divided by time for a particular particle energy and air density.

Referring to FIG. 1, an exemplary particle therapy system according to the conventional art is shown. The particle therapy system 100 can include a particle therapy delivery system 105, a particle therapy planning system 110, and the like. The particle therapy delivery system 105 can include, but is not limited to, a beam source 125, one or more particle therapy delivery controllers 130, and one or more beam transport systems 135. The particle therapy delivery system 105 can further include a gantry 140, beam current and profile monitor 145, beam applicator 150 and patient table 155 disposed in each of one or more treatment rooms 160. The beam source 125 can be coupled to the gantry 140, beam applicator 150, and beam current and profile monitor 145 of the respective treatment room 160 by the beam transport system 135. The beam transport system 135 can be configured to focus and shape energy beams and guide them to the gantries 140 in the one or more treatment rooms 160. The gantry 140 can rotate about a patient on the patient table 155 to deliver the energy beam at different angles while minimizing the need to reposition the patient. The patient table 155 can include a sophisticated patient positioning system that moves in one or more directions to position patients. The beam applicator 150 can be configured to scan a particle beam about a target area of the patient. The beam current and profile monitor 145 can include an array of detectors and a sampling processor configured to sample charge values between ionization chamber plates of the array of ionization detectors to determine accumulation, beam current, and beam profile parameters of or associated with charged particles (e.g., ions, heavy ions, protons, electrons, or the like) of the particle stream.

The one or more particle therapy delivery controllers 130 can be configured to control the operation of the beam source 125, beam transport system 135, gantries 140, beam current and profile monitors 145, beam applicators 150 and/or patient tables 155. One or more computing devices comprising the particle therapy planning system 110 can also be configured to generate patient particle therapy treatment plans. The one or more computing devices of the particle therapy planning system 110 and/or the particle therapy delivery system 130 can include one or more processors, one or more memories, one or more network interfaces, and one or more input/output devices, such as keyboards, pointing devices, displays and/or the like, coupled together by one or more busses. The one or more computing devices 110, 130 can be any type of computing device, including but not limited to embedded processors, desktop Personal Computers (PCs), laptop PCs, server computer, virtual machine, cloud computing platform, or the like. The one or more computing devices can be coupled directly to each other and or can be coupled through one or more networks 165, including Local Area Networks (LAN), Wide Area Networks (WAN), the Internet or the like. Alternatively or in addition, one or more of the computing devices can be combined together and/or integral to one or more other subsystems of the particle therapy system 100.

In many cases, energy can be delivered to the target tissue with sub-millimeter precision, while mostly sparing normal tissue, ultimately leading to killing cells in the target tissue. However, the tumor cells' ability to escape the cell killing effects of radiation and/or to develop resistance mechanisms can counteract the cell killing effect of particle therapy, potentially limiting the therapeutic effect of particle therapy. Furthermore, delivery of ultra-high dose rate radiation within a short time period in particle therapy treatment techniques, sometimes referred to as FLASH treatment, is believed to spare normal tissue from radiation-induced toxicity. Thus, the treatment outcome regarding the target and toxicity to the surrounding tissue not only depends on physical parameters, such as dose, but also depends on treatment delivery time. Currently, treatment plans are based on physical dose distribution, which can be displayed in three-dimensions. Most treatment plans only use dosimetric endpoint goals as a proxy for biological impact, such as, "do not exceed max spinal cord dose of x." The particle therapy treatment plan specifies a dose distribution, such as the dose at each spot, voxel or the like. The dose distribution is then converted to machine parameters, typically through a lookup table, for the control of the beam source 125 and beam applicator 150 based on spot lists (i.e., spot-wise dose control). Conventional particle therapy treatment plans prescribe the MUs for each of a plurality of spots, voxels of the like (e.g., three dimensional dose distribution) covering a target volume of the unhealthy tissue. These spots may have different MUs. Each MU value can be precisely delivered to each spot utilizing MU counters that provide feedback to beam applicator 150 when the spot MUs are delivered, and then the particle beam is moved to a next spot. In some embodiments of particle therapy system 100, spots are treated in separate layers of the treatment volume, where each layer is a different particle energy. The planned source beam current and resulting MU rate are constant for each layer. Delivering a single beam current to spots in a single layer with different MU values has constraints such as minimum spot treatment time per spot, while at the same time delivering the correct MU amount to each spot. For spots in a given energy layer with a constant MU rate, this minimum spot treatment time per spot limits the MU rate for high MU spots due to low MU spots. Another consideration is that the beam applicator 150 does not use time to determine when the spot MUs are delivered, so that some variability in the beam source current is tolerated.

To utilize new treatment techniques such as FLASH, new particle therapy treatment plans look to deliver the treatment over a short time period utilizing high dose rates or proportionally high MU rates. To maximize the MU rates for high MU spots, it is desirable to specify different MU rates for individual spots in the treatment volume, referred to as spot-wise MU rates (proportional to beam output current), along with the MUs per spot. These different MU rates may be planned, then specified based on therapeutic benefits as well as minimizing total treatment time. Furthermore, it is necessary to minimize variability and errors in the magnitude of the beam output current to ensure the delivery of the correct dose rate or MU rate. Such variability and errors in the beam output current may originate from the beam source or beam transport system. Therefore, there is a continuing need for improved techniques for delivery of the particle therapy treatment plan.

SUMMARY OF THE INVENTION

The present technology may best be understood by referring to the following description and accompanying drawings that are used to illustrate embodiments of the present technology directed toward particle therapy closed-loop feedback spot-wise beam current control systems and methods.

In one embodiment, a particle therapy delivery system can include a beam monitor, a closed-loop feedback beam control module and a beam source. The beam monitor can be configured to determine an output beam current. The closed-loop feedback control module can be configured to generate an adjusted source beam current set point based on a treatment plan beam current for a present spot and the determined output beam current for the present spot. The beam source can be configured to generate a beam source current based on the adjusted source beam current set point.

In another embodiment, a particle therapy closed-loop feedback beam control method can include receiving a treatment plan's beam current parameters for a present spot and a determined output beam current of the present spot. An adjusted source beam current set point can be generated based on the received treatment plan's beam current of the present spot and the determined output beam current of the present spot. A beam source current can be adjusted based on the adjusted source beam current set point.

In another embodiment, the particle therapy closed-loop feedback control method can include receiving a treatment plan's parameters for a plurality of spots. An adjusted source beam current set point can be generated based on beam current parameters of the received treatment plan's parameters for a present spot and a determined output beam current of the present spot. A beam source current can be generated based on the adjusted source beam current set point. An output of the source beam current can be directed based on beam spatial parameters of the received treatment plan's beam parameters. Measurement unit (MU) rate and MU accumulation of the present spot can be measured. The output beam current of the present spot can be determined based on the measured measurement unit rate and MU accumulation of the present spot.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

Embodiments of the present technology are illustrated by way of example and not by way of limitation, in the figures of the accompanying drawings and in which like reference numerals refer to similar elements and in which.

DETAILED DESCRIPTION OF THE INVENTION

Figure 1:
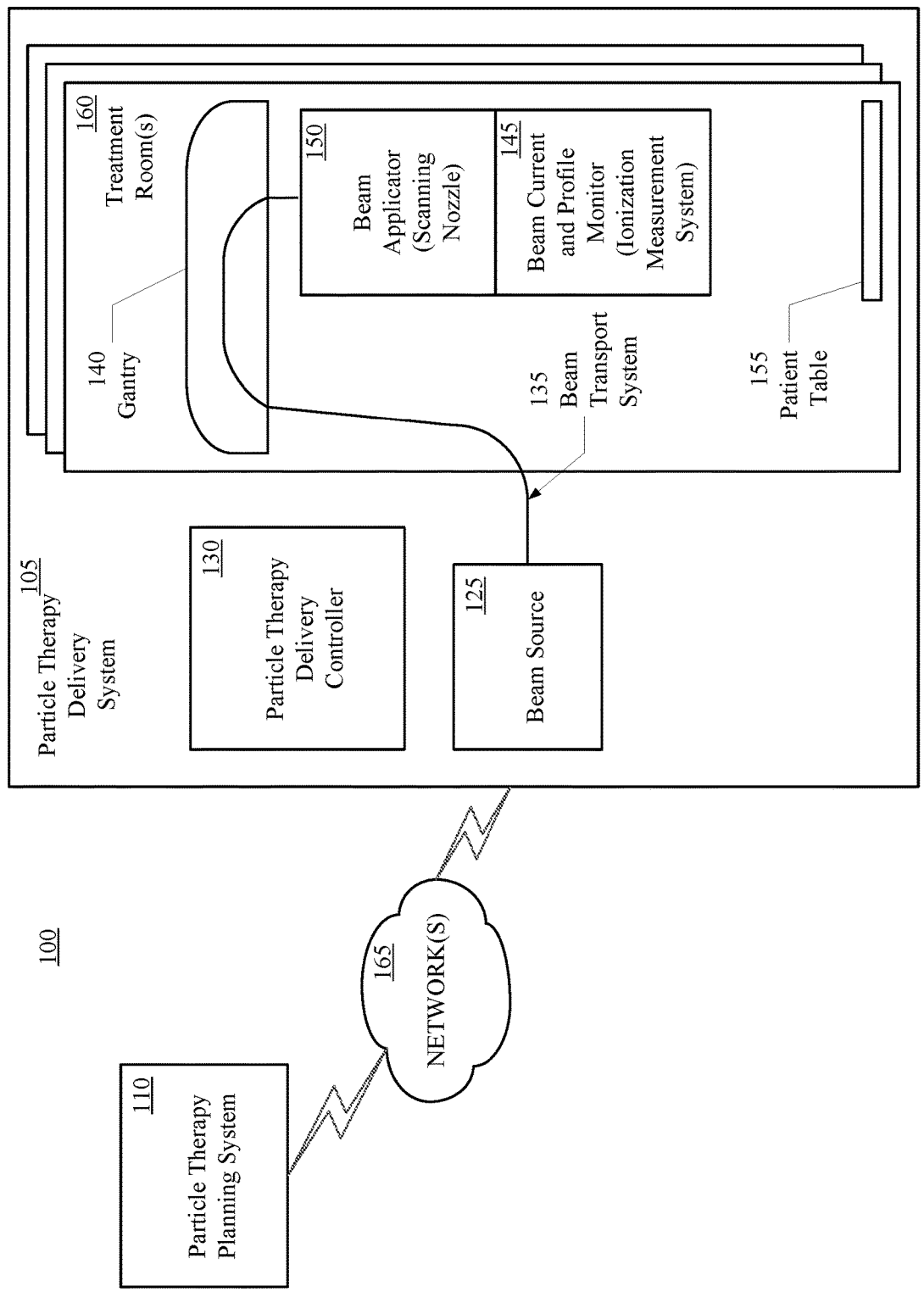
FIG. 1 shows an exemplary particle therapy system according to the conventional art.

Reference will now be made in detail to the embodiments of the present technology, examples of which are illustrated in the accompanying drawings. While the present technology will be described in conjunction with these embodiments, it will be understood that they are not intended to limit the technology to these embodiments. On the contrary, the invention is intended to cover alternatives, modifications and equivalents, which may be included within the scope of the invention as defined by the appended claims. Furthermore, in the following detailed description of the present technology, numerous specific details are set forth in order to provide a thorough understanding of the present technology. However, it is understood that the present technology may be practiced without these specific details. In other instances, well-known methods, procedures, components, and circuits have not been described in detail as not to unnecessarily obscure aspects of the present technology.

Some embodiments of the present technology which follow are presented in terms of routines, modules, logic blocks, and other symbolic representations of operations on data within one or more electronic devices. The descriptions and representations are the means used by those skilled in the art to most effectively convey the substance of their work to others skilled in the art. A routine, module, logic block and/or the like, is herein, and generally, conceived to be a self-consistent sequence of processes or instructions leading to a desired result. The processes are those including physical manipulations of physical quantities. Usually, though not necessarily, these physical manipulations take the form of electric or magnetic signals capable of being stored, transferred, compared and otherwise manipulated in an electronic device. For reasons of convenience, and with reference to common usage, these signals are referred to as data, bits, values, elements, symbols, characters, terms, numbers, strings, and/or the like with reference to embodiments of the present technology.

It should be borne in mind, however, that these terms are to be interpreted as referencing physical manipulations and quantities and are merely convenient labels and are to be interpreted further in view of terms commonly used in the art. Unless specifically stated otherwise as apparent from the following discussion, it is understood that through discussions of the present technology, discussions utilizing the terms such as "receiving," and/or the like, refer to the actions and processes of an electronic device such as an electronic computing device that manipulates and transforms data. The data is represented as physical (e.g., electronic) quantities within the electronic device's logic circuits, registers, memories and/or the like, and is transformed into other data similarly represented as physical quantities within the electronic device.

In this application, the use of the disjunctive is intended to include the conjunctive. The use of definite or indefinite articles is not intended to indicate cardinality. In particular, a reference to "the" object or "a" object is intended to denote also one of a possible plurality of such objects. The use of the terms "comprises," "comprising," "includes," "including" and the like specify the presence of stated elements, but do not preclude the presence or addition of one or more other elements and or groups thereof. It is also to be understood that although the terms first, second, etc. may be used herein to describe various elements, such elements should not be limited by these terms. These terms are used herein to distinguish one element from another. For example, a first element could be termed a second element, and similarly a second element could be termed a first element, without departing from the scope of embodiments. It is also to be understood that when an element is referred to as being "coupled" to another element, it may be directly or indirectly connected to the other element, or an intervening element may be present. In contrast, when an element is referred to as being "directly connected" to another element, there are not intervening elements present. It is also to be understood that the term "and/or" includes any and all combinations of one or more of the associated elements. It is also to be understood that the phraseology and terminology used herein is for the purpose of description and should not be regarded as limiting.

Figure 2:
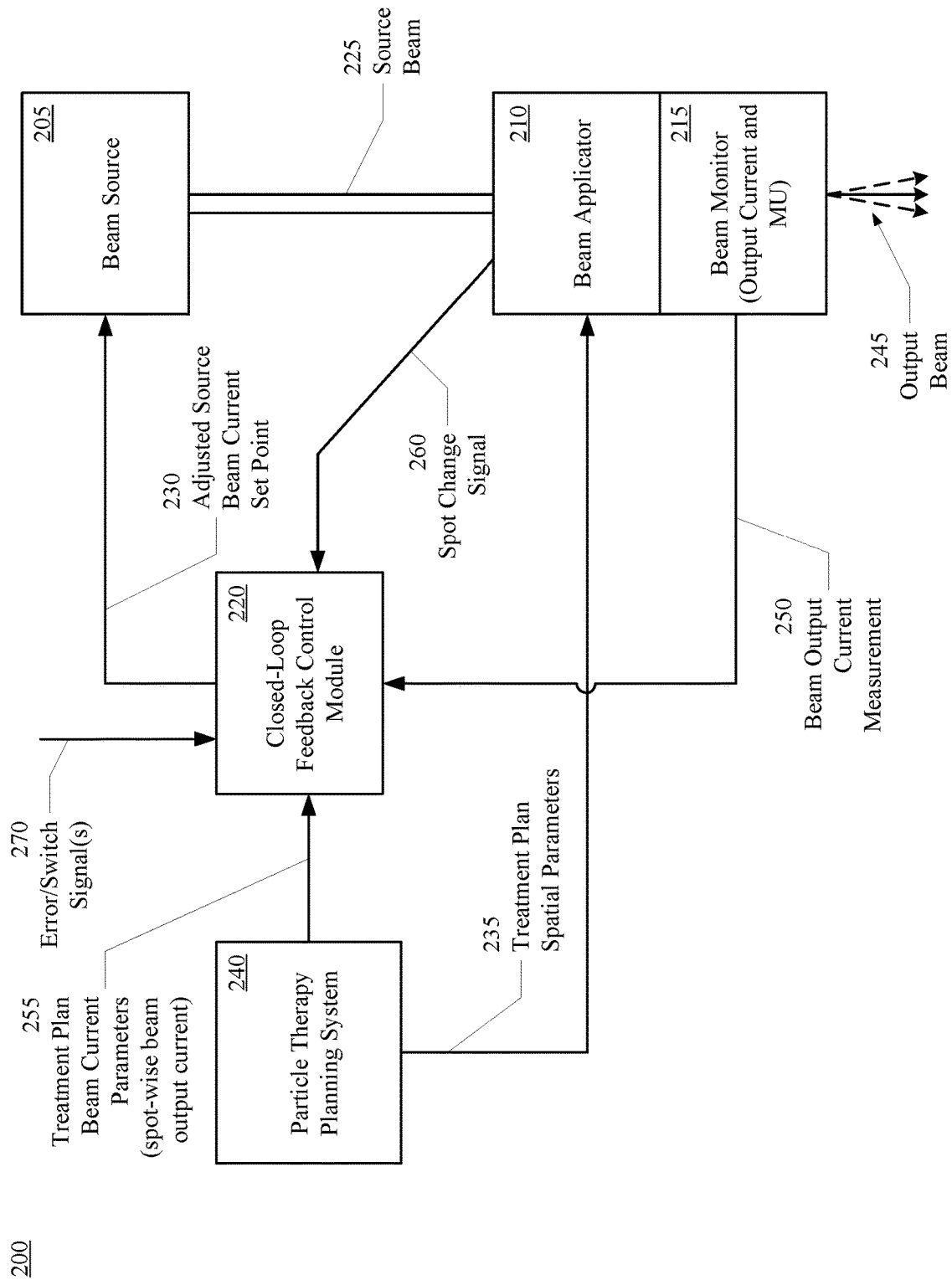
FIG. 2 shows a particle therapy closed-loop feedback beam control system, in accordance with aspects of the present technology.

Referring now to FIG. 2, a particle therapy delivery system 200, in accordance with aspects of the present technology, is shown. The particle therapy delivery system 200 can be a spatial dose distribution modulated particle therapy system, wherein the local dose is varied across the target volume. Depending upon the treatment modality, the degrees of freedom available for spatial dose distribution modulation can include, but are not limited to, beam shaping (collimation), beam weighting (beam scanning) and angle of incidence (beam geometry). In one implementation, the particle therapy system 200 can be a high dose rate particle therapy system, such as but not limited to a proton FLASH particle therapy system. High dose rate particle therapy delivers high doses of radiation at high speeds, or short irradiation times, of 40 Gy/s and above. Exemplary FLASH therapy treatment plans can indirectly specify delivering treatment to an extended target volume in one second or less by specifying one or more measurement unit (MU) rates. Studies have shown that delivering particle therapy at such high dose rates allows comparable tumor control while sparing the healthy tissue to reduce unintended toxicities. In one implementation, the proton FLASH particle therapy system 200 can be a spot scanning proton FLASH particle therapy system.

The particle therapy delivery system 200 can include a beam source 205, a beam applicator 210, a beam monitor 215 and a closed-loop feedback control module 220. The particle therapy delivery system 200 can further include a particle therapy planning system 240, a patient imaging system (not shown) and/or the like. The beam source 205 can be configured to generate a source beam 225 based on an adjusted source beam current set point 230. The adjusted source beam current set point 230 controls the beam source 205 to generate the source beam 225. In one implementation, the beam source 205 can be a cyclotron. In one implementation, the beam source 205 can be controlled by the adjusted source beam current set point 230 to adjust the source beam current differently for each of a plurality of individual spots. The beam applicator 210 can be configured to shape the source beam and direct the beam to individual spots based on beam spatial parameters of a treatment plan 235. In one implementation, the beam spatial parameters 235 can control magnet field deflectors of the beam applicator 210 to direct the output beam 245 toward each of a plurality of spot locations in the target tissue. The beam monitor 215 can be configured to measure measurement units (MUs) and MU rate of the output beam 245. The MU rate can be converted into a output beam current measurement 250. In one implementation, the beam applicator 210 can also determine a spot change signal 260 that can indicate when a present spot is finished being irradiated, and signal the next spot is starting.

In one implementation, a sampling processor of the beam monitor 215 can sample charge values between ionization chamber plates in an array of ionization detectors to determine MUs, time and position parameters of or associated with a charged particle (e.g., ion, proton, electron or the like) stream. In one implementation, the beam monitor 215 can extract MU information (e.g., spot MUs) delivered for a given time (e.g., spot timing), and spatial information (e.g., spot position) in a two-dimensional (2D) plane, at each of one or more given depths of interest (e.g., one or more layers).

The closed-loop feedback control module 220 can be configured to determine the adjusted source beam current set point 230 from treatment plan beam current parameters 255, the beam output current measurement 250, and spot change signal 260. In one implementation, the closed-loop feedback control module 220 can receive the spot-wise beam current parameters 255 of a treatment plan from the particle therapy planning system 240. In one implementation, the closed-loop feedback control module 220 can implement a proportional-integral-derivative (PID) controller. The PID controller can continuously calculate an error value e(t) as a difference between a nominal beam current of the treatment plan (e.g., desired set point (SP)) and the measured output beam current (e.g., measured process variable (PV)). The closed-loop feedback control module 220 can generate an adjusted output current based on one or more computed error values, then estimate an equivalent adjusted source beam current set point 230 from the adjusted output current and a beam current transmission loss lookup table. The beam current transmission loss lookup table can be based on estimated beam current losses from source beam 225 to output beam 245 as a function of energy. In other implementations, the closed-loop feedback control module 220 can implement a proportional integral (PI) controller, a proportional (P) controller, or the like. In one implementation, the closed-loop feedback control module 220 can be implemented as computing device-executable instructions (e.g., computer program) that are stored in computing device-readable media (e.g., computer memory) and executed by a computing device (e.g., processor). The closed-loop feedback control module 220 can adjust the source beam current periodically via the adjusted source beam current set point 230. The beam applicator 210 can determine when a planned number of MUs are delivered for each spot, and when this number is delivered, can shift the beam from a current spot to a next spot and update the spot change signal 260. The combination of the beam applicator 210 and the closed-loop feedback control module 220 advantageously minimizes errors in the delivered beam output current or MU rate for the present spot. In contrast, a conventional particle therapy delivery system does not minimize errors in the beam output current or MU rate in a spot-wise fashion.

For some implementations where the closed-loop feedback control module 220 implements a PID or PI controller, the closed-loop feedback control module 220 can receive one or more error state signals 270 indicating when the beam source 205 is in an error state, and stops the error integration to avoid integral error windup. For some implementations, one or more switch state signals 270 can also indicate when the beam source 205 is intended to switch off the source beam 225 (either due to scanning logic or an error), and this can cause the closed-loop feedback control module 220 to stop the error integration to avoid integral error windup in the module 220.

For some implementations the closed-loop feedback control module 220 can also include a feedforward element to set a new adjusted source beam current when the spot-wise treatment plan's beam current parameters 255 change, possibly when the present spot changes. This minimizes the delay in setting a new adjusted source beam current set point 230, versus waiting to correct for the error between the new source beam current set point and the measured beam output current. A new spot then receives a new set beam output current with minimal delay, and achieves the new spot's MU rate specification with minimal delay.

Figure 3:
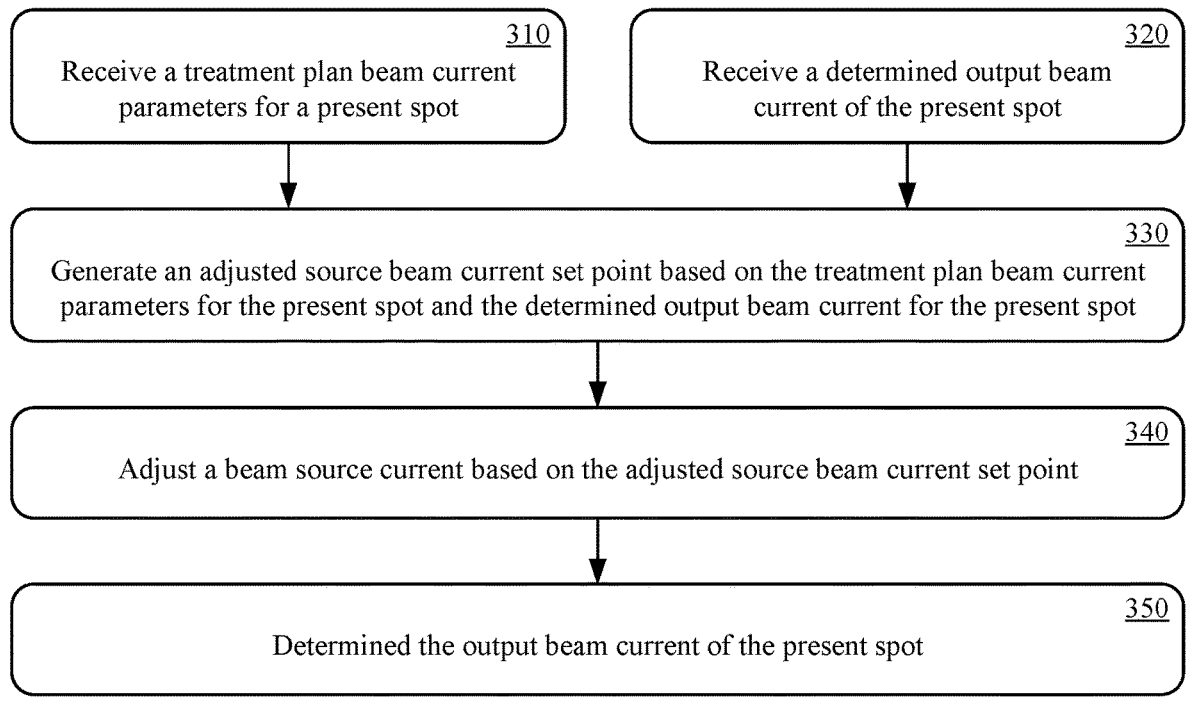
FIG. 3 shows a particle therapy closed-loop feedback beam control method, in accordance with aspects of the present technology.

Referring now to FIG. 3, a particle therapy closed-loop feedback beam control method, in accordance with aspects of the present technology, is shown. The particle therapy closed-loop beam control method can include receiving one or more treatment plan beam current parameters for a present spot, at 310. The treatment plan beam current parameters can include a particle energy, measurement units (MU) per spot, and MU rate per spot converted into a beam output current based on energy. In one implementation, the treatment plan beam current parameters can be received from a particle therapy planning system. In one implementation, the treatment plan beam current parameters can comprise, but are not limited to, FLASH treatment plan beam output current, proton beam output current, pencil beam scanning beam output current, spot scanning beam output current or the like. At 320, a determined output beam current of a present spot can be received. In one implementation, the determined output beam output current of the present spot can be received from a beam monitor of a particle therapy delivery system. At 330, an adjusted source beam current set point can be generated based on the received treatment plan beam current parameters for the present spot and the determined output beam current of the present spot. Optionally, the adjusted source beam current set point can be generated based on the received treatment plan beam current parameters for the present spot, the determined output beam current of the present spot and a loss lookup table. In one implementation, the adjusted source beam current set point can include corresponding adjusted machine parameters for controlling a beam source of the particle therapy delivery system. In one implementation, the adjustment of the source beam current set point may be implemented by a proportional-integral-derivative (PID) control algorithm, a proportional integral (PI) control algorithm, proportional (P) control algorithm or the like. In one implementation, the adjustment of the source beam current set point may be implemented as computing device-executable instructions (e.g., computer program) that are stored in computing device-readable media (e.g., computer memory) and executed by a computing device (e.g., processor). In one implementation, the adjustment parameter o(t) can be calculated by the PID controller based on the error function e(t) as $$o(t) = \lambda_p \cdot e(t) + \lambda_i \int_0^t e(t) d\tau + \lambda_d \frac{de(t)}{dt}$$

where $\lambda_p$ corresponds to the proportional gain, $\lambda_i$ is the integral gain and $\lambda_d$ the derivative gain of the PIC controller. At 340, a beam source current can be adjusted based on the adjusted source beam current set point. At 350, the output beam current of the present spot can be determined. In one implementation, accumulated MUs can be monitored of the present spot, and the spot can be changed when MUs for the present spot reach a threshold for the present spot. The process of 310 through 350 can be iteratively performed for each of a plurality of spots for a treatment plan.

Figure 4:
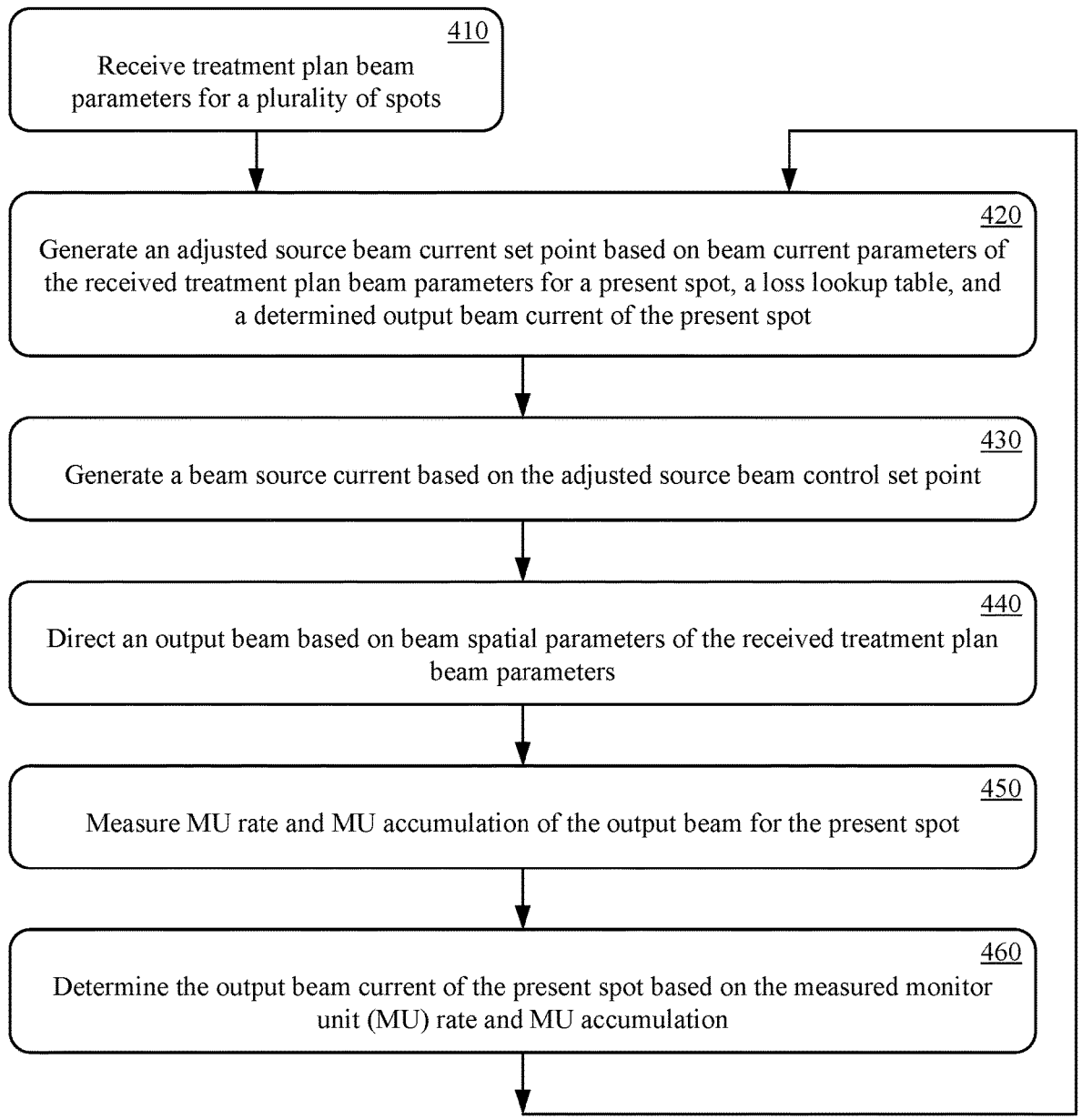
FIG. 4 shows a particle therapy closed-loop feedback beam control method, in accordance with aspects of the present technology.

Referring now to FIG. 4, a particle therapy closed-loop feedback beam control method, in accordance with aspects of the present technology, is shown. The particle therapy closed-loop feedback beam control method can include receiving treatment plan beam parameters for each of a plurality of spots, at 410. In one implementation, the treatment plan beam parameters can include beam current parameters and beam spatial parameters. In one implementation, the beam current parameters can be derived from treatment plan MU rates for each spot received from a particle therapy planning system, then converted into treatment plan beam currents based on particle energy and air density. In one implementation, the treatment plan beam current parameters can comprise, but are not limited to, FLASH treatment plan beam currents, proton treatment plan beam currents, pencil beam scanning treatment plan beam currents, spot scanning treatment plan beam currents or the like. At 420, an adjusted beam source current set point can be generated based on beam current parameters of the received treatment plan beam parameters for a present spot, a system loss lookup table, and a determined output beam current of the present spot. The determined output beam current of the present spot can be determined at 460 as described below. In one implementation, the received treatment plan beam current parameters can be embodied in treatment plan machine parameters received from a particle therapy planning system. The adjusted source beam current set point can be generated from the treatment plan beam current parameters and the determined output beam current received from a beam monitor of a particle therapy delivery system. In one implementation, the received treatment plan beam current parameters can include treatment plan MU rate parameters that are converted to treatment plan beam output current, which is used to generate the adjusted source beam current set point. The adjusted source beam current set point can be generated by proportional-integral-derivative (PID), proportional integral (PI), proportional (P) or the like closed-loop feedback. At 430, a beam source current can be generated based on the adjusted source beam current set point. In one implementation, the adjusted source beam current set point can be embodied as adjusted machine parameters for controlling a beam source. In one implementation, one or more of the beam intensity, beam shape, beam weight and beam angle of incidence of charged particles (e.g., ions, proton, electron or the like) generated by a beam source can be adjusted based on the adjusted source beam current set point. At 440, an output beam can be directed based on beam spatial parameters of the received treatment plan beam parameters. In one implementation, beam spatial parameters of the received treatment plan beam parameters can control a beam applicator to direct an output pencil beam, spot beam or the like over a target volume in a patient. At 450, a MU rate and MU accumulation of the output beam for the present spot can be measured. In one implementation, a beam monitor can measure the charged particle (e.g., ions, proton, electron) current of the output particle stream. At 460, the output beam current of the present spot can be determined from the measured MU rate and MU accumulation. The determined output beam current of the present spot can be utilized at 420 to generate the adjusted source beam current set point in the closed-loop feedback method. The method advantageously minimizes errors in the output beam current based on the present spot. In contrast, a conventional particle therapy delivery system does not minimize errors in the beam output current in a spot-wise fashion.

For some implementations where the adjusted source beam current set point can be generated by proportional-integral-derivative (PID) or proportional integral (PI) closed-loop feedback, an error state signal can be received indicating when the beam source is in an error state, and stops the error integration to avoid integral error windup. For some implementations, a switching signal can also indicate when the beam source is intended to switch off the output beam and can also stop the error integration to avoid integral error windup.

Figure 5:
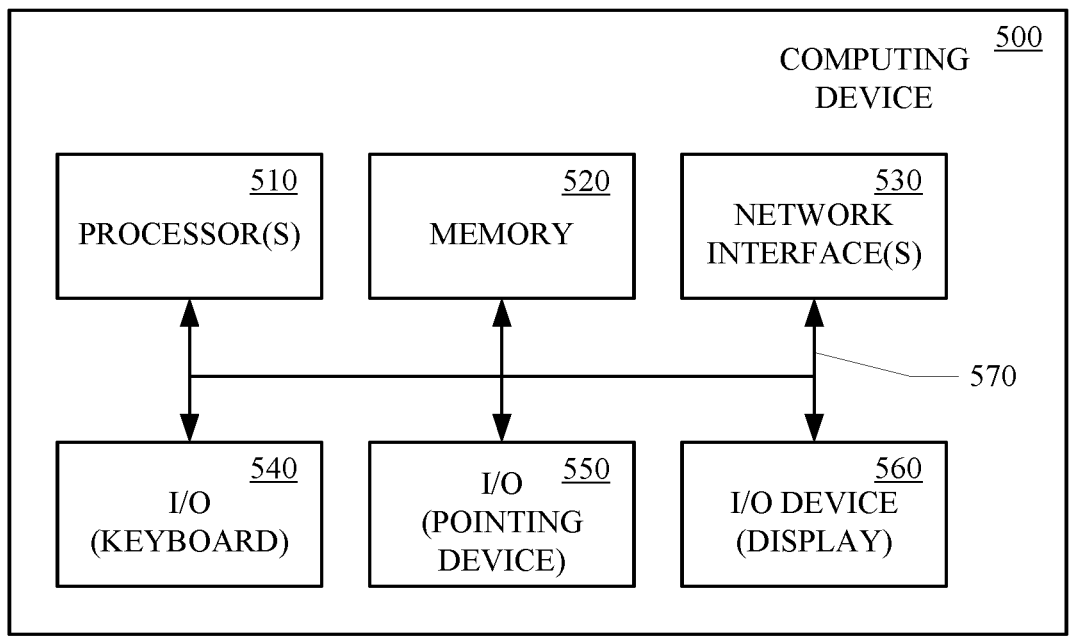
FIG. 5 shows an exemplary computing device for implementing aspects of the present technology.

Referring now to FIG. 5, a computing device for implementing one or more aspects of the present technology is shown. The computing device 500 can include one or more processors 510, one or more memories 520, one or more network interface 530, and one or more input/output devices 540-560 such as keyboards, pointing devices, displays and/or the like, coupled together by one or more busses 570. The computing device 500 can be any type of computing device, including but not limited to embedded processors, desktop Personal Computers (PCs), laptop PCs, server computer, virtual machine, cloud computing platform, or the like. One or more software routines (e.g., computing device executable instructions) stored in the one or more memories (e.g., computing device readable media) 520, when executed by the one or more processors 510, can implement the particle therapy closed-loop feedback beam control systems and methods as described above.

In accordance with aspects of the present technology, a particle therapy delivery system can include a beam output current and measurement unit (MU) monitor, a closed-loop feedback control module, a beam source, and a particle therapy treatment plan. The output current and measurement unit (MU) monitor can be configured to measure MUs and MU rate of the actual source beam current delivered to a plurality of spots. The output current and measurement unit (MU) monitor can convert the MU rate into a beam output current measurement with a lookup table and passes this to the closed-loop feedback control module. The closed-loop feedback control module can be configured to determine an adjusted source beam current set point based on a nominal spot-wise treatment plan beam current and the measured output beam current. This adjusted source beam current set point is calculated to minimize the difference between planned and measured beam output current for each spot, in terms of reaction time to changing treatment plan beam current for a new spot as well as rejecting disturbances to the output beam current. The control module can also receive a signal to indicate when sufficient MUs are delivered to each spot, based on the treatment plan, and when to switch to the next spot and its corresponding treatment plan beam current. The treatment plan can include MUs and MU rate per spot, and a nominal output beam current per spot can be calculated from the MU rate per spot. The closed-loop feedback control can include a beam transmission loss look up table to convert between output beam current and source beam current. The beam transmission loss look up table can be based on estimated beam current losses from source beam to output beam as a function of energy.

In accordance with aspects of the present technology, a particle therapy closed-loop feedback spot-wise beam current control method can include receiving spot-wise treatment plan beam current and measured output beam current. An adjusted source beam current set point can be generated based on the treatment plan beam current for the present spot and the measured output beam current. A source beam current can be adjusted based on the adjusted source beam current set point to minimize error in the output beam current.

The foregoing descriptions of specific embodiments of the present technology have been presented for purposes of illustration and description. They are not intended to be exhaustive or to limit the present technology to the precise forms disclosed, and obviously many modifications and variations are possible in light of the above teaching. The embodiments were chosen and described in order to best explain the principles of the present technology and its practical application, to thereby enable others skilled in the art to best utilize the present technology and various embodiments with various modifications as are suited to the particular use contemplated. It is intended that the scope of the invention be defined by the claims appended hereto and their equivalents.

What is claimed is:

1. A particle therapy delivery system comprising:
a beam monitor configured to determine an output beam current;
a closed-loop feedback control module configured to generate an adjusted source beam current set point based on a treatment plan beam current for a present spot, the determined output beam current for the present spot, and a loss lookup table including estimated beam current losses from a source beam to an output beam as a function of energy; and
a beam source configured to generate a beam source current based on the adjusted source beam current set point.

2. The particle therapy delivery system of claim 1, wherein the output beam current comprises a charged particle, proton, or electron particle stream.

3. The particle therapy delivery system of claim 1, wherein the treatment plan beam current comprises FLASH particle therapy treatment plan beam current.

4. The particle therapy delivery system of claim 1, wherein the closed-loop feedback control module is further configured to determine the treatment plan beam current from a particle therapy treatment plan.

5. The particle therapy delivery system of claim 1, wherein the closed-loop feedback control module comprises a proportional-integral-derivative (PID), proportional integral (PI), or proportional (P) controller configured to determine the adjusted source beam current set point based on a difference between the treatment plan beam current and the determined output beam current, and the loss lookup table.

6. The particle therapy delivery system of claim 5, wherein the closed-loop feedback control module comprises a PID or PI controller configured to stop an error integration in response to a signal indicating that the beam source is in an error state.

7. The particle therapy delivery system of claim 5, wherein the closed-loop feedback control module comprises a PID or PI controller configured to stop an error integration in response to a signal indicating that the beam source intends to switch off the source beam.

8. The particle therapy delivery system of claim 5, wherein the closed-loop feedback control module further comprises a feedforward element configured to adjust the source beam current when the treatment plan beam current changes to minimize delay in setting the output beam current for a new spot.

9. The particle therapy delivery system of claim 1, further comprising a beam applicator configured to direct the beam source current based on spatial parameters of a treatment plan.

10. A particle therapy closed-loop feedback beam control method comprising:
   receiving a treatment plan beam current for a present spot;
   receiving a determined output beam current of the present spot;
   generating an adjusted source beam current set point based on the received treatment plan beam current of the present spot, the determined output beam current of the present spot, and a loss lookup table including estimated beam current losses from a source beam to an output beam as a function of energy;
   adjusting a beam source current based on the adjusted source beam current set point; and
   determining the output beam current of the present spot.

11. The particle therapy closed-loop feedback beam control method according to claim 10, wherein:
   the treatment plan beam current is specified by a spot-wise FLASH particle therapy treatment plan; and
   the treatment plan beam current comprises a charged particle, proton, or electron particle stream.

12. The particle therapy closed-loop feedback beam control method according to claim 10, wherein the adjusted source beam current set point is generated by proportional-integral-derivative (PID), proportional integral (PI), or proportional (P) feedback based on the treatment plan beam current of the present spot and the determined output beam current of the present spot.

13. A particle therapy closed-loop feedback control method comprising:
   receiving treatment plan parameters for a plurality of spots;
   generating an adjusted source beam current set point based on beam current parameters of the received treatment plan parameters for a present spot, a determined output beam current of the present spot, and a loss lookup table including estimated beam current losses from a source beam to an output beam as a function of energy;
   generating a beam source current based on the adjusted source beam current set point;
   directing an output of the source beam current based on beam spatial parameters of the received treatment plan parameters;
   measuring measurement unit (MU) rate and MU accumulation of the present spot; and
   determining the output beam current of the present spot based on the measured measurement unit (MU) rate and MU accumulation of the present spot.

14. The particle therapy closed-loop feedback control method according to claim 13, wherein the output beam comprises a charged particle, proton, or electron particle stream.

15. The particle therapy closed-loop feedback control method according to claim 13, wherein a treatment plan including the treatment plan parameters comprises a FLASH particle therapy treatment plan.

16. The particle therapy closed-loop feedback control method according to claim 13, wherein the adjusted source beam current set point is generated by proportional-integral-derivative (PID), proportional integral (PI), or proportional (P) feedback based on a difference between the beam current parameters of the received treatment plan parameters for the present spot and the determined output beam current of the present spot.

17. The particle therapy closed-loop feedback control method of claim 16, further comprising stopping integration of feedback error in response to receiving a signal indicating that the beam source is in an error state.

18. The particle therapy closed-loop feedback control method of claim 16, further comprising stopping integration of feedback error in response to receiving a signal indicating switching off the beam source.

19. The particle therapy closed-loop feedback control method of claim 16, further comprising feeding forward the beam current parameters of the received treatment plan parameters to minimize a delay in setting a new adjusted source beam current set point for a new spot.

* * * * *